US010435565B2

(12) United States Patent
Borst et al.

(10) Patent No.: US 10,435,565 B2
(45) Date of Patent: Oct. 8, 2019

(54) METHINE DYES

(71) Applicant: LANXESS Deutschland GmbH, Cologne (DE)

(72) Inventors: Hans-Ulrich Borst, Elsdorf (DE); Stephan Michaelis, Odenthal (DE); Frank Linke, Cologne (DE)

(73) Assignee: LANXESS Deutschland GmbH, Cologne (DE)

( * ) Notice: Subject to any disclaimer, the term of this patent is extended or adjusted under 35 U.S.C. 154(b) by 0 days.

(21) Appl. No.: 16/197,608

(22) Filed: Nov. 21, 2018

(65) Prior Publication Data

US 2019/0161618 A1    May 30, 2019

(30) Foreign Application Priority Data

Nov. 24, 2017   (EP) .................................... 17203529

(51) Int. Cl.
| | | |
|---|---|---|
| C07D 401/06 | (2006.01) |
| C09B 23/10 | (2006.01) |
| C08K 5/00 | (2006.01) |
| C08K 5/3432 | (2006.01) |
| C08J 3/215 | (2006.01) |

(52) U.S. Cl.
CPC .......... *C09B 23/105* (2013.01); *C07D 401/06* (2013.01); *C08J 3/215* (2013.01); *C08K 5/0041* (2013.01); *C08K 5/3432* (2013.01); *C08J 2333/12* (2013.01)

(58) Field of Classification Search
CPC .... C07D 401/06; C09B 23/105; C09B 23/102

USPC ....................... 546/277.4; 8/659; 252/301.22
See application file for complete search history.

(56) References Cited

U.S. PATENT DOCUMENTS

2003/0003396 A1    1/2003   Berneth et al.

FOREIGN PATENT DOCUMENTS

JP    5314734 A    2/1978

OTHER PUBLICATIONS

Wurthner, F. et al.: Design, synthesis , and evaluation of a Dye library : Glass-forming and solid-state luminescent Merocyanines for functional materials. Angewandte Chemie, Int. Ed., vol. 38, pp. 1649-1652, 1999.*
Wurthner, F. et al.: Molecular design of thermally stable glass-forming Merocyanine dyes. J. Inform. Recording, vol. 25, pp. 69-86, 2000.*
Park, S. et al.: Synthesis of Merocyanine dyes based on Pyridinones. J. Ind. Eng. Chem., vol. 11, pp. 688-691, 2005.*
European Search Report from corresponding European Application No. 17203529, dated Mar. 13, 2018, three pages.
Schwetlick, B.K. Organikum, VEB Duetscher Verlag der Wissenschafter, Berlin, 15 edition 1977, pp. 260, 253, 674.
Wuerthner, Frank, DMF in Acetic Anhydride: A Useful Reagent for Multiple-Component Syntheses of Merocyanine Dyes:, Synthesis 1999, No. 12, Thieme Stuttgart, pp. 2103-2113.

* cited by examiner

*Primary Examiner* — Charanjit Aulakh

(57) ABSTRACT

Novel red methine dyes, methods for the preparation thereof, and use thereof for dyeing plastics, especially vinyl polymers, provide red colourings with improved colour strengths and improved colour brilliance.

17 Claims, No Drawings

METHINE DYES

The present invention relates to novel methine dyes, methods for the preparation thereof and use thereof for dyeing plastics.

BACKGROUND INFORMATION

Although there are already numerous red dyes on the market for colouring plastics, demand still exists for novel dyes with improved properties. Dyes of different classes of dyes are available which are suitable for colouring plastics in shades of red.

Known soluble red dyes which are used for plastic colouring are, e.g. Solvent Red 135 (Macrolex® Rot EG) (C.I 564120), Solvent Red 179 (Macrolex® Rot E2G) (C.I 564150), Solvent Red 52 (Macrolex® Rot 5B) (C.I. 68210) and Solvent Red 195 (Macrolex® Rot B).

However, the colouristic properties of existing red dyes are not always sufficient for the average technical requirements in the use for colouring plastics. In particular, there is a demand for red dyes for the bulk colouration of plastics which are enhanced with regard to their colour intensity and brilliance, as compared with what is currently available.

SUMMARY OF THE INVENTION

The present invention relates to novel methine dyes of the formula (I)

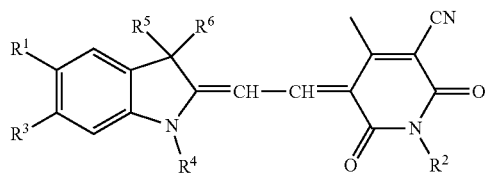

in which
$R^1$ is hydrogen, halogen, COOH or COOR$^7$,
$R^2$ is hydrogen or alkyl,
$R^3$ is hydrogen, halogen, CN, COOH or COOR$^8$,
$R^4$ is alkyl or phenyl
and
$R^5$ and $R^6$ are each independently alkyl
and
$R^7$ and $R^8$ are each independently alkyl.

DESCRIPTION OF THE EMBODIMENTS

Alkyl in the definitions of $R^2$ and $R^4$ to $R^8$ refer to a straight-chain or branched alkyl radical that is unsubstituted or mono- or polysubstituted by the same or different substituents, for example to straight-chain or branched $C_1$-$C_6$-alkyl, preferably straight-chain or branched $C_1$-$C_4$-alkyl, especially methyl, ethyl, n- and isopropyl, which may in each case be optionally mono- or polysubstituted by the same or different substituents, for example by halogen, such as chlorine, bromine or fluorine, and also by —OH, —CN, —NH$_2$ or $C_1$-$C_6$-alkoxy.

Halogen in the definitions of $R^1$ and $R^3$ refer for example to fluorine, chlorine or bromine.

In an alternative embodiment, the present invention relates to methine dyes of the formula (I),
in which
$R^1$ is hydrogen, halogen, COOH or COOR$^7$,
$R^2$ is hydrogen or alkyl,
$R^3$ is hydrogen, halogen, CN, COOH or COOR$^8$,
$R^4$ is alkyl or phenyl,
and
$R^5$ and $R^6$ are each independently alkyl
and
$R^7$ and $R^8$ are each independently alkyl,
with the condition that $R^1$ and $R^3$ are not both hydrogen.

Preference is given to dyes of the formula (I),
in which
$R^1$ is hydrogen, halogen, COOH or COOR$^7$,
$R^2$ is hydrogen or is $C_1$-$C_4$-alkyl, which is optionally mono- to trisubstituted, identically or differently, by halogen and/or hydroxyl,
$R^3$ is hydrogen, halogen, CN, COOH or COOR$^8$,
$R^4$ is $C_1$-$C_4$-alkyl or phenyl
$R^5$ and $R^6$ are each independently $C_1$-$C_4$-alkyl,
and
$R^7$ and $R^8$ are each independently $C_1$-$C_4$-alkyl.

In an alternative embodiment, preference is also given to dyes of the formula (I),
in which
$R^1$ is hydrogen, halogen COOH or COOR$^7$,
$R^2$ is hydrogen, or is $C_1$-$C_4$-alkyl, which is optionally mono- to trisubstituted, identically or differently, by halogen and/or hydroxyl,
$R^3$ is hydrogen, halogen, CN, COOH or COOR$^8$,
$R^4$ is $C_1$-$C_4$-alkyl or phenyl
$R^5$ and $R^6$ are each independently $C_1$-$C_4$-alkyl
and
$R^7$ and $R^8$ are each independently $C_1$-$C_4$-alkyl,
with the condition that $R^1$ and $R^3$ are not both hydrogen.

Particular preference is given to dyes of the formula (I),
in which
$R^1$ is hydrogen, fluorine, chlorine, COOH or COOR$^7$,
$R^2$ is hydrogen, methyl, ethyl, n-propyl, isopropyl, n-butyl, isobutyl or tert-butyl, hydroxymethyl, hydroxyethyl or CF$_3$,
$R^3$ is hydrogen, fluorine, chlorine, CN or COOR$^8$,
$R^4$ is methyl or phenyl,
$R^5$ and $R^6$ are each independently methyl or ethyl
and
$R^7$ and $R^8$ are each independently methyl or ethyl.

Particular preference is also alternatively given to dyes of the formula (I),
in which
$R^1$ is hydrogen, fluorine, chlorine, COOH or COOR$^7$,
$R^2$ is hydrogen, methyl, ethyl, n-propyl, isopropyl, n-butyl, isobutyl or tert-butyl, hydroxymethyl, hydroxyethyl or CF$_3$,
$R^3$ is hydrogen, fluorine, chlorine, CN or COOR$^8$,
$R^4$ is methyl or phenyl,
$R^5$ and $R^6$ are each independently methyl or ethyl
and
$R^7$ and $R^8$ are each independently methyl or ethyl,
with the condition that $R^1$ and $R^3$ are not both hydrogen.

Very particular preference is given to dyes of the formula (I),
in which
$R^1$ is hydrogen, fluorine chlorine or COOCH$_3$,
$R^2$ is n-butyl, isobutyl, tert-butyl or hydroxyethyl,
$R^3$ is hydrogen, fluorine or chlorine
and
$R^4$, $R^5$ and $R^6$ are each methyl.

Very particular preference is also given to dyes of the formula (I), in which
R¹ is hydrogen, fluorine, chlorine or COOCH₃,
R² is n-butyl, isobutyl, tert-butyl or hydroxyethyl,
R³ is hydrogen, fluorine or chlorine
and,
R⁴, R⁵ and R⁶ are each methyl,
with the condition that R¹ and R³ are not both hydrogen.

Dyes of the formula (I) can exist as stereoisomers. Formula (I) particularly includes the following four E and Z isomers of the formulae (Ia) to (Id):

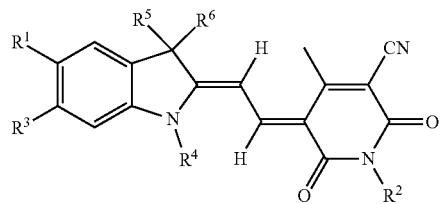
(Ia)

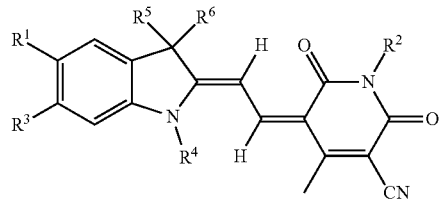
(Ib)

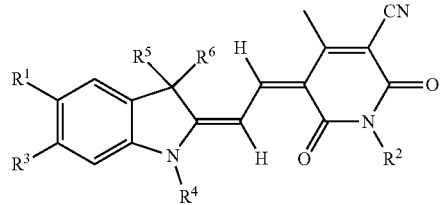
(Ic)

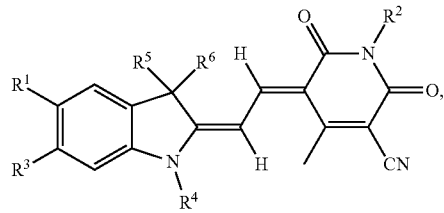
(Id)

wherein the substituents R¹ to R⁶ have the general and preferred definitions specified for formula (I).

In a further alternative embodiment, the present invention relates to methine dyes of the formula (Ia), in which the substituents R¹ to R⁶ have the general and preferred definitions specified for formula (I).

Using the dyes of the formula (I) according to the invention, red colouration of plastics can be achieved, which are surprisingly characterized by both greater colour strength and at the same time greater colour brilliance compared with the colourations achievable with the known dyes.

It is possible using the dyes according to the invention to significantly outperform the property profiles achieved to date of known red dyes for plastic colouration.

The present invention further relates to the use of the dyes of the formula (I) according to the invention for the bulk colouration of plastics. The dyes according to the invention can be used here individually or in any desired mixture with one another.

Bulk colouration in this case is understood to mean in particular methods in which the dye is incorporated into the molten plastic material, e.g. with the aid of an extruder, or in which the dye is already added to the starting components for preparing the plastic, e.g. to monomers prior to polymerization.

Particularly preferred plastics are thermoplastics, for example vinyl polymers, polyesters and polycarbonates. Very particular preference is given to vinyl polymers, especially polystyrene and polyester, especially polyethylene terephthalate and polycarbonate.

Suitable vinyl polymers are polystyrene, styrene-acrylonitrile copolymers, styrene-butadiene copolymers, styrene-butadiene-acrylonitrile terpolymers, polymethacrylate and polyvinyl chloride among others.

Suitable polyesters are, for example, polyethylene terephthalates, polybutadiene terephthalates, polycarbonates and cellulose esters.

The plastics to be coloured may be present individually or as mixtures with one another, as plastic materials or melts.

When used for the bulk colouration of plastics, the dyes (I) according to the invention are preferably applied in finely divided form for application, wherein dispersants may be, but do not have to be, used concomitantly.

When used for the bulk colouration of plastics, the dyes (I) according to the invention can be used for example directly in the process of the plastic preparation after the polymerization is complete. In this case, at least one dye (I) according to the invention is preferably mixed in dry form or ground with the plastic granules and this mixture is plasticized and homogenized for example on mixing rollers or in screws. However, the dyes (I) according to the invention may also be added to the molten liquid material and homogeneously distributed by stirring. The material precoloured in this way may then be further processed as usual, e.g. by spinning to give bristles, threads etc. or by extrusion or in injection molding processes to give moldings.

The present invention further relates to a method for bulk colouration of plastics, characterized in that at least one dye of formula (I) is mixed with at least one molten plastic and this mixture is subsequently homogenized.

Since the dyes (I) are resistant to polymerization catalysts, particularly peroxides, it is also possible to add the dyes (I) according to the invention to the monomeric starting materials for the plastic preparation, e.g. of polymethyl methacrylate (PMMA) and then to polymerize in the presence of polymerization catalysts. For this purpose, the dye is preferably dissolved in the monomeric components or mixed intimately with them.

The present invention further relates to a method for bulk colouration of polymethyl methacrylate (PMMA), characterized in that at least one dye of formula (I) is mixed with or dissolved in at least one methyl methacrylate monomer and this mixture or solution is then polymerized in the presence of at least one polymerization catalyst.

The dyes of the formula (I) according to the invention for colouring the plastics mentioned, especially polyamide, are used preferably in amounts from 0.0001 to 1% by weight, especially 0.01 to 0.5% by weight, based on the amount of polymer.

By adding pigments insoluble in the polymers, for example titanium dioxide, it is possible to obtain corresponding useful covered colourations.

Titanium dioxide may be used in an amount from 0.01 to 10% by weight, preferably 0.1 to 5% by weight, based on the amount of polymer.

The present invention further relates to a method for the bulk colouration of plastics, wherein at least one dye of the formula (I) is mixed in dry form or is ground with at least one plastic, preferably in the form of granules, and this mixture is plasticized and homogenized, e.g. on mixing rollers or in screws.

However, the dyes (I) according to the invention may also be added to the molten liquid material and homogeneously distributed by stirring. It is likewise possible to add the dyes (I) according to the invention to the monomeric starting components in the plastic preparation and then to polymerize.

The material pre-coloured in this way may then be further processed as usual, e.g. by spinning to give bristles, threads etc. or by extrusion or in injection molding processes to give moldings.

By means of the method according to the invention, transparent or covered brilliant red colourations which also have very good heat and light resistances are obtained.

To carry out the method according to the invention, it is also possible to use mixtures of the dyes of the formula (I) according to the invention with other dyes and/or inorganic and/or organic pigments.

The present invention further relates to a method for preparing the dyes of the formula (I) according to the invention.

The dyes of the formula (I) according to the invention may be prepared by reacting at least one aldehyde of the formula (II)

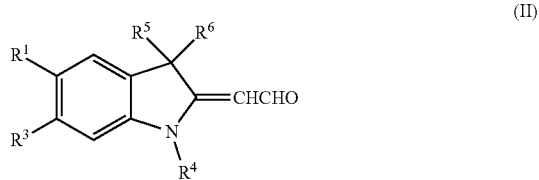

in which
$R^1$, $R^3$, $R^4$, $R^5$ and $R^6$ have the general and preferred definitions specified for formula (I),
with at least one pyridone derivative of the formula (III)

in which
$R^2$ has the general and preferred definition specified for formula (I).

The aldehyde of the formula (II) can exist as stereoisomers. The formula (II) includes both possible E and Z forms.

The method for preparing the dyes (I) according to the invention by reacting the aldehydes of the formula (II) with the pyridone derivatives of the formula (III) may be carried out in a manner known per se.

The method for preparing the dyes (I) according to the invention is carried out generally at a temperature in the range from −10 to 180° C., preferably from 0 to 100° C. and particularly preferably from 10 to 90° C.

The method for preparing the dyes (I) according to the invention is carried out generally at a pressure from 900 to 1100 hPa, preferably at ambient pressure. Ambient pressure is understood to mean an air pressure in the range from about 925 hPa to 1070 hPa.

The method for preparing the dyes (I) according to the invention can be carried out in the presence of at least one solvent. Suitable solvents are those from the series of alcohols and formamides for example. The method for preparing the dyes (I) according to the invention is preferably carried out in the presence of at least one alcohol from the series of methanol, ethanol, propanol, and/or at least one formamide from the series of dimethylformamide and diethylformamide, particularly preferably in the presence of methanol and/or dimethylformamide.

The method for preparing the dyes (I) according to the invention is carried out in the presence of at least one base. Suitable bases are, for example, alkali metal hydroxides and alkali metal alkoxides. Preference is given to using lithium hydroxide, sodium hydroxide, potassium hydroxide and/or potassium tert-butoxide, particularly preferably sodium hydroxide and/or potassium tert-butoxide.

In general, the method for preparing the dyes (I) according to the invention is carried out such that the aldehyde (II) is firstly initially charged and the pyridone derivative (III) is added and, after reaction is complete, the compounds of the formula (I) are isolated. The isolation can be carried out by customary processes, preferably by filtration. The reaction product obtained can optionally be worked-up by further method steps such as washing and drying.

To carry out the method, generally 0.8 to 1.5 mol of pyridone derivative (III) is used per mole of aldehyde (II). Preferably, 0.9 to 1.1 mol of pyridone derivative (III) is used per mole of aldehyde (II) and particularly preferably 1 mol of pyridone derivative (III) is used per mole of aldehyde (II).

Pyridone derivatives of the formula (III) are known and can be purchased as commercial products from Alfa Acer for example.

The aldehydes of the formula (II) are also known and can be prepared, for example, in a two-stage synthesis in a manner known to those skilled in the art. Here, in a first stage a), at least one indole derivative of the formula (IV)

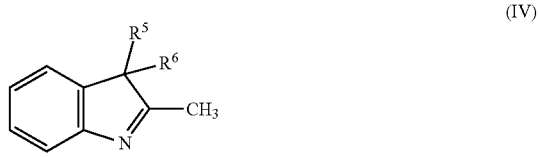

in which
$R^5$ and $R^6$ have the general and preferred definitions specified for formula (I),
is reacted with at least one alkylating reagent and subsequently, in a second stage b), the intermediate of the first stage is reacted with at least one formylation reagent.

Reactions of the kind described in stage b) are known in the literature under the name of Vilsmeier reaction.

Generally, the reaction in stage a) is carried out such that the indole derivative of the general formula (IV) is initially charged and the alkylating agent is added optionally in the presence of a solvent.

The first stage a) of the reaction is carried out generally at a temperature in the range from 10 to 80° C., preferably from 20 to 70° C. and particularly preferably from 30 to 60° C.

The reaction in stage a) is carried out generally at a pressure from 900 to 1100 hPa, preferably at ambient pressure. Ambient pressure is understood to mean an air pressure in the range from about 925 hPa to 1070 hPa.

The reaction in stage a) may be carried out in the presence of at least one solvent. Suitable solvents are those from the series of alcohols and water for example. The reaction in stage a) is preferably carried out in the presence of water as solvent.

In principle, all known alkylating reagents are suitable as alkylating reagent (see e.g. B. K. Schwetlick, Organikum, VEB Deutscher Verlag der Wissenschaften, Berlin, 15th edition 1977, pages 260, 253, 674), such as dimethyl sulfate, methyl iodide or diazomethane. Preference is given to the use of dimethyl sulfate.

In general, at least one mole of alkylating reagent is used per mole of indole derivative. Depending on the structure of the indole derivative, corresponding to the above stoichiometry, even higher molar amounts may be used. Preferably, 0.9 to 1.1 mol, particularly preferably 1 mol of alkylating reagent is used per mole of indole derivative (IV).

The intermediate prepared in stage a) can be isolated by customary methods, by filtration for example. The intermediate prepared in stage a) is preferably further reacted directly without isolation in the subsequent stage b).

In general, the reaction in stage b) is carried out in such a manner that the alkylated compound from the first stage a) in the form of the reaction solution obtained is initially charged and the formylation reagent is added, optionally in the presence of at least one solvent, and subsequently the aldehyde of the formula (II) thus prepared is precipitated, optionally by the addition of a suitable amount of a suitable precipitant, and the aldehyde of the formula (II) is then isolated by customary methods, by filtration for example.

The reaction in stage b) is carried out generally at a temperature in the range from 10 to 80° C., preferably from 20 to 70° C. and particularly preferably from 30 to 60° C.

The reaction in stage b) is carried out generally at a pressure from 900 to 1100 hPa, preferably at ambient pressure. Ambient pressure is understood to mean an air pressure in the range from about 925 hPa to 1070 hPa.

The reaction in stage b) may be carried out in the presence of at least one solvent. Suitable solvents are formamides for example. Preference is given to dimethylformamide and diethylformamide, particular preference being given to the use of dimethylformamide. When using dimethylformamide, it is particularly preferable to use this in excess wherein the dimethylformamide then serves as formylation reagent and solvent at the same time.

The formylation reagent used in stage b) is generally a mixture of at least one formamide and at least one phosphoric acid chloride.

Preferred formamides are dimethylformamide, diethylformamide and dibutylformamide.

A preferred phosphoric acid chloride is phosphorus oxychloride.

The formylation reagent used is particularly preferably a mixture of dimethylformamide and phosphorus oxychloride.

In general, at least one mole of formylation reagent, preferably 1.1 to 1.5 mol and particularly preferably 1.1 to 1 mol, is used per mole of alkylated compound from stage 1.

Suitable precipitants are, for example, alcohols such as methanol and/or ethanol.

The precipitant used is preferably methanol and/or ethanol, especially methanol.

The indole derivatives of the formula (IV) are known to those skilled in the art. They may be prepared in a manner known per se in a two-stage synthesis by reacting an aniline derivative of the formula (V)

(V)

in which $R^1$ and $R^3$ have the general and preferred definition specified for formula (I), with a diazotization reagent and subsequent reaction with ring closure with a ketone of the formula (VI)

(VI)

in which $R^5$ and $R^6$ have the general and preferred definition specified for formula (I).

The diazotization reaction is generally carried out by initially charging the aniline derivative and adding the diazotization reagent at a temperature in the range from 0 to 10° C. at standard pressure in an aqueous medium.

In principle, any suitable diazotization reagent is an option as diazotization reagent. Preference is given to using an aqueous sodium nitrite solution.

In general, the diazotization reagent is used in an amount of at least two moles based on the aniline derivative (V).

The ring closure reaction with the ketone of the formula (VI) is carried out in a manner known per se in a one-pot reaction by reducing the diazonium salt of the aniline derivative (V) to the hydrazone and by reacting the hydrazone with the ketone of the general formula (VI), preferably at a temperature in the range from 40 to 100° C., preferably in aqueous solution, and subsequently by isolating and washing the indole derivative of the formula (IV) by customary methods, preferably filtration.

The aniline derivatives of the formula (V) and the ketones of the formula (VI) are known and can be purchased as commercial products, from Alfa Acer or Sigma-Aldrich for example.

The invention is elucidated but not limited by the following examples, in which the parts are by weight and percentage values are percent by weight (% by weight).

EXAMPLES

Example 1

Preparation of the inventive compound of the formula (I)

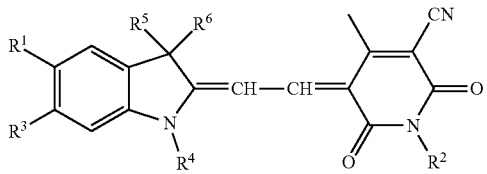

where $R^1$=COOCH$_3$; $R^2$=C$_4$H$_9$; $R^3$=H and $R^4$, $R^5$ and $R^6$=CH$_3$ In 160 ml of acetic anhydride, 25.9 g (0.1 mol) of aldehyde of the formula (II), where $R^1$=COOCH$_3$; $R^3$=H and $R^4$, $R^5$ and $R^6$=CH$_3$, and 20.6 g (0.1 mol) of N-butyl-6-hydroxy-3-cyano-4-methyl-2-pyridone and 5 g of ammonium chloride were introduced. Subsequently, the reaction mixture was heated to a temperature of 105° C. and stirred for ca. 6 hours. The mixture was then cooled to 25° C. and 200 ml of methanol were added and the reaction product was isolated on a Nutsche filter. The filter cake was washed with ca. 600 ml of methanol and ca. 4000 ml of water at a temperature of 90° C. The washed product was dried in a vacuum drying cabinet at a temperature of 80° C. and a pressure of 200 hPa.

Yield: 38.2 g (corresponds to 85% of theory), melting point 261° C.

Examples 2 to 4

Preparation of inventive compounds of the formula (I) in which the substituents $R^1$ to $R^6$ have the definitions listed in Table 1.

TABLE 1

| Example | $R^1$ | $R^2$ | $R^3$ | $R^4$ | $R^5$ | $R^6$ |
|---|---|---|---|---|---|---|
| 2 | H | C$_4$H$_9$ | H | CH$_3$ | CH$_3$ | CH$_3$ |
| 3 | Cl | C$_4$H$_9$ | H | CH$_3$ | CH$_3$ | CH$_3$ |
| 4 | H | C$_4$H$_9$ | F | CH$_3$ | CH$_3$ | CH$_3$ |

The preparation and work-up of the compounds of examples 2 to 4 were each carried out in analogy to example 1 but with the following deviations:

Example 2

90 ml of acetic acid and 160 ml of acetic anhydride were initially charged. Instead of the aldehyde used in example 1, 20.1 g (0.1 mol) of the aldehyde of formula (II) where $R^1$ and $R^3$=H and $R^4$, $R^5$ and $R^6$=CH$_3$ and also 4 g of ammonium chloride were used. After cooling to 25° C., 170 ml of methanol were added, the reaction product isolated on a Nutsche filter and the filter cake washed with 100 ml of methanol and ca. 400 ml of water at a temperature of 90° C.

Yield: 35.2 g (corresponds to 90% of theory), melting point 254° C.

Example 3

190 ml of acetic acid were initially charged. Instead of the aldehyde used in example 1, 23.6 g (0.1 mol) of aldehyde of formula (II) where $R^1$=Cl; $R^3$=H and $R^4$, $R^5$ and $R^6$=CH$_3$ and 6 g of ammonium chloride were used. After cooling to 25° C., 250 ml of methanol were added, the reaction product isolated on a Nutsche filter and the filter cake washed with 150 ml of methanol and ca. 600 ml of water at a temperature of 90° C.

Yield: 33.2 g (corresponds to 78% of theory), melting point 273° C.

Example 4

190 ml of acetic acid were initially charged. Instead of the aldehyde used in example 1, 21.9 g (0.1 mol) of aldehyde of formula (II) where $R^1$=H; $R^3$=F and $R^4$, $R^5$ and $R^6$=CH$_3$ and also 2.5 g of ammonium chloride were used. After cooling to 25° C., 200 ml of methanol were added, the reaction product isolated on a Nutsche filter and the filter cake washed with 150 ml of methanol and ca. 600 ml of water at a temperature of 90° C.

Yield: 33.8 g (corresponds to 86% of theory), melting point 253° C.

Preparation of the Precursors

Example 5

Preparation of an aldehyde of the formula (II)

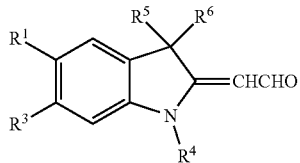

where $R^1$=COOCH$_3$; $R^3$=H and $R^4$, $R^5$ and $R^6$=CH$_3$ a) diazotization:

139.9 g of p-aminobenzoic acid were introduced to 270 g of 30% hydrochloric acid and the mixture was cooled to 0° C. by externally cooling. Subsequently, 174 g of a 40% aqueous solution of sodium nitrite were added. The mixture was stirred for 30 minutes and then the excess nitrite was removed with ca. 0.5 g of amidosulfonic acid.

b) Preparation of the hydrazone and ring closure:

A mixture of 250 g of water and 660 g of sodium hydrogensulfite, in the form of a 39% aqueous solution, was adjusted to a pH of 6.5 with 80 g of a 40% aqueous sodium hydroxide solution. Over the course of ca. 30 minutes, the diazotization solution prepared in stage a) was added, while maintaining a pH of ca. 6.5 by addition of 100 g of a 40% aqueous sodium hydroxide solution. Subsequently, the reaction mixture was stirred at a temperature of 40° C. for ca. 1 hour. Subsequently, 560 g of 96% sulfuric acid and then 86.1 g of methyl isopropyl ketone were added dropwise. The reaction mixture was heated to 70° C. and stirred for ca. 4 hours. The reaction mixture was subsequently heated to 80° C. and then stirred again for ca. 4 hours. The reaction mixture was then cooled to 25° C. and the pH was adjusted to 6.5 with ca. 800 g of a 40% aqueous sodium hydroxide solution. The reaction mixture was stirred for 30 minutes and the reaction product was then isolated on a Nutsche filter and washed with 2 liters of water.

c) Preparation of the aldehyde:

The moist press cake of the ring-closed product from stage b) was introduced into 1200 g of water. The pH was then adjusted to 10 with ca. 70 g of a 40% aqueous sodium hydroxide solution. Over the course of 1 hour, 325 g of dimethyl sulfate were added dropwise maintaining a pH here of ca. 8.5 by addition of 200 g of a 40% aqueous sodium hydroxide solution. The reaction mixture was heated to 40° C. and stirred for ca. 5 hours. The reaction mixture was subsequently heated to 60° C. and then stirred for a further 1 hour. The reaction mixture was then left to stand whereupon a phase separation took place within 1 hour. The aqueous phase was then removed. Residual water was removed from the organic phase under reduced pressure at 80° C. and 20 hPa. 310 g of dimethylformamide were then added dropwise to the organic phase. Subsequently, 263 g of phosphorus oxychloride were added at 40° C. over the course of 3 hours and the reaction mixture was stirred for 5 hours. The mixture was then cooled to 20° C. and 160 g of methanol were added. The pH was then adjusted to 11 with ca. 200 g of a 40% aqueous sodium hydroxide solution. The reaction mixture was subsequently stirred for 60 minutes and then the reaction product was isolated on a Nutsche filter and washed with 160 g of methanol and 2000 g of water. The washed product was dried in a vacuum drying cabinet at a temperature of 80° C. and a pressure of 200 hPa.

Yield: 176.3 g (corresponds to 68% of theory)

Example 6

Preparation of an aldehyde of the formula (II) where $R^1$=Cl, $R^3$=H and $R^4$, $R^5$ and $R^6$=CH$_3$.
a) diazotization:
The preparation of the diazotization solution was carried out as specified in example 5 a), but 268 g of 30% hydrochloric acid were employed and 127.6 g of 4-chloroaniline were used instead of p-aminobenzoic acid.
b) preparation of the hydrazone and ring closure:
The preparation of the hydrazone was carried out in analogy to example 5 a), but the diazotization solution from Example 6 a) was used.
c) Preparation of the aldehyde:
The moist press cake of the ring-closed product from stage b) was introduced into 1200 g of water. The pH was then adjusted to 10 with ca. 5 g of a 40% aqueous sodium hydroxide solution. Over the course of 1 hour, 153 g of dimethyl sulfate were added dropwise maintaining a pH here of ca. 8.5 by addition of 90 g of a 40% aqueous sodium hydroxide solution. The reaction mixture was heated to 40° C. and stirred for ca. 5 hours. The reaction mixture was subsequently heated to 60° C. and then stirred for a further 1 hour. The reaction mixture was then left to stand whereupon a phase separation took place within 1 hour. The aqueous phase was then removed. Residual water was removed from the organic phase under reduced pressure at 80° C. and 20 hPa. 275 g of dimethylformamide were then added dropwise to the organic phase. Subsequently, 116 g of phosphorus oxychloride were added at 40° C. over the course of 3 hours and the reaction mixture was stirred for 5 hours. The mixture was then cooled to 20° C. and 160 g of methanol were added. The pH was then adjusted to 11 with ca. 180 g of a 40% aqueous sodium hydroxide solution. The reaction mixture was subsequently stirred for 60 minutes and then the reaction product was isolated on a Nutsche filter and washed with 160 g of methanol and 2000 g of water. The washed product was dried in a vacuum drying cabinet at a temperature of 80° C. and a pressure of 200 hPa.

Yield: 141.4 g (corresponds to 60% of theory)

Example 7

Preparation of an aldehyde of the formula (II) were $R^1$=H, $R^3$=F and $R^4$, $R^5$ and $R^6$=CH$_3$.

a) diazotization:
The preparation of the diazotization was carried out as specified in example 5 a), but 375 g of 30% hydrochloric acid were employed and 155.5 g of 3-fluoroaniline were used instead of p-aminobenzoic acid.
b) Preparation of the hydrazone and ring closure:
A mixture of 250 g of water and 918 g of sodium hydrogensulfite, in the form of a 39% aqueous solution, was adjusted to a pH of 6.5 with 120 g of a 40% aqueous sodium hydroxide solution. Over the course of ca. 30 minutes, the diazotization solution prepared in stage a) was added, while maintaining a pH of ca. 6.5 by addition of 140 g of a 40% aqueous sodium hydroxide solution. Subsequently, the reaction mixture was stirred at a temperature of 40° C. for ca. 1 hour. Subsequently, 776 g of 96% sulfuric acid and then 120.4 g of methyl isopropyl ketone were added dropwise. The reaction mixture was heated to 70° C. and stirred for ca. 4 hours. The reaction mixture was subsequently heated to 80° C. and then stirred again for ca. 4 hours. The reaction mixture was then cooled to 25° C. and the pH was adjusted to 6.5 with ca. 1150 g of a 40% aqueous sodium hydroxide solution. The reaction mixture was stirred for 30 minutes and the reaction product was then isolated on a Nutsche filter and washed with 2 liters of water.
c) Preparation of the aldehyde:
The moist press cake of the ring-closed product from stage b) was introduced into 1200 g of water. The pH was then adjusted to 10 with ca. 10 g of a 40% aqueous sodium hydroxide solution. Over the course of 1 hour, 194 g of dimethyl sulfate were added dropwise maintaining a pH here of ca. 8.5 by addition of 120 g of a 40% aqueous sodium hydroxide solution. The reaction mixture was heated to 40° C. and stirred for ca. 5 hours. The reaction mixture was subsequently heated to 60° C. and then stirred for a further 1 hour. The reaction mixture was then left to stand whereupon a phase separation took place within 1 hour. The aqueous phase was then removed. Residual water was removed from the organic phase under reduced pressure at 80° C. and 20 hPa. 350 g of dimethylformamide were then added dropwise to the organic phase. Subsequently, 147 g of phosphorus oxychloride were added at 40° C. over the course of 3 hours and the reaction mixture was stirred for 5 hours. The mixture was then cooled to 20° C. and 160 g of methanol were added. The pH was then adjusted to 11 with ca. 200 g of a 40% aqueous sodium hydroxide solution. The reaction mixture was subsequently stirred for 60 minutes and then the reaction product was isolated on a Nutsche filter and washed with 160 g of methanol and 2000 g of water. The washed product was dried in a vacuum drying cabinet at a temperature of 80° C. and a pressure of 200 hPa.

Yield: 169.1 g (corresponds to 55% of theory)

List of Substances Purchased

| Name | Molecular weight | Cas. No. | Content | Manufacturer |
|---|---|---|---|---|
| p-Aminobenzoic acid | 137.2 | 150-13-0 | 98 | Sigma-Aldrich |
| Methyl isopropyl ketone | 86.1 | 563-80-4 | 99 | Sigma-Aldrich |
| Isopropyl methyl ketone | | | | |
| 4-Chloroaniline | 127.6 | 106-47-8 | 98 | Sigma-Aldrich |
| 3-Fluoroaniline | 111.1 | 372-19-0 | 99 | Alfa Acer |
| 2-(1,3,3--Trimethylindolin-2 ylidene)-acetaldehyde | 201.3 | 84-83-3 | 97 | Sigma-Aldrich |

Spectroscopic Measurements

The results of the UV/VIS measurements and absorption values for the inventive compounds of Examples 1 to 4 and those of the non-inventive comparative compounds are listed in Table 2.

The UV/VIS absorption spectra of the inventive and non-inventive compounds were all measured in the solvent 1-methoxy-2-propyl acetate (CAS No. 108-65-6).

TABLE 2

| Example/ comparison | Inventive | Absorption maximum UV/VIS spectrum[1] | E 1/1 value[2] |
|---|---|---|---|
| Example 1 | Yes | 526 nm | 2672 |
| Example 2 | Yes | 524 nm | 2890 |
| Example 3 | Yes | 521 nm | 3173 |
| Example 4 | Yes | 520 nm | 2874 |
| Macrolex ® Rot EG | No | 496 nm | 160 |
| Macrolex ® Rot E2G | No | 473 nm | 290 |
| Macrolex ® Rot B | No | 528 nm | 900 |
| Macrolex ® Rot 5 B | No | 539 nm | 350 |

The E1/1 value specified is a hypothetical absorption value. Initially measured is the absorbance of a solution of the respective sample in 1-methoxy-2-propyl acetate in a cuvette of 1 cm path length, wherein the concentration of the solution is selected such that the absorption value observed at the absorption maximum is about 1. The value determined is then converted to a concentration of 1 percent by weight whereby the E1/1 value is obtained.

Dyes which have both colour strength and high colour brilliance are characterized in that they have absorption bands in the visible spectral range with low peak widths at half maximum and at the same time high extinction coefficients at the wavelength of the absorption maximum are present.

The calculated peak widths at half maximum (WHM) and molar extinction coefficients at the absorption maximum ($\varepsilon$ max) for the inventive and non-inventive compounds are listed in Table 3.

TABLE 3

| Example/ comparison | Inventive | WHM* [nm] | $\varepsilon$ max [l/mol * cm] |
|---|---|---|---|
| 1 | Yes | 47 | 124000 |
| 2 | Yes | 46 | 127000 |
| 3 | Yes | 40 | 128000 |
| 4 | Yes | 46 | 121000 |
| Macrolex ® Rot EG | No | 126 | 6700 |
| Macrolex ® Rot E2G | No | 117 | 9600 |
| Macrolex ® Rot B | No | 84 | 38000 |

*The peak width at half maximum specifies in this case the width of the distribution at half the maximum value of the distribution. A differentiation is generally made between the full width at half maximum (FWHM) and the half width at half maximum (HWHM). The peak widths at half maximum specified in Table 3 correspond to the full width at half maximum (FWHM).

Determination of the Colour Strength and Brilliance

To determine the colour strength and brilliance of the inventive samples of examples 1 to 4 and the non-inventive comparative example, each sample was subjected to a colour measurement according to the procedure specified below.

500 g of polystyrene coloured with 2% by weight titanium dioxide was mixed with 0.10% by weight dye powder by shaking in a sealed plastic bag. From the homogeneous granular dye mixture, sample plates of 4 cm×6 cm×0.2 cm were prepared on an injection moulding machine at 240° C. mass temperature, 20 bar dynamic pressure and 60° C. moulding temperature.

After not less than ten injection cycles, sample plates were withdrawn for colour measurement and left to stand at room temperature for at least 1 hour.

Using a d/8° spectral photometer, reflectance measurements were carried out on the sample plates. The colour strength and residual colour differences were determined in accordance with DIN 55986, and the brilliance in accordance with DIN EN ISO 11664-4.

The results of the colour brilliance and colour strength measurements for the inventive and non-inventive compounds are listed in Table 4.

TABLE 4

| Example/ comparison | Inventive | Colour strength | Brilliance dC |
|---|---|---|---|
| 1 | Yes | 131 | 8.8 |
| 2 | Yes | 135 | 8.9 |
| 3 | Yes | 141 | 10.7 |
| 4 | Yes | 132 | 8.8 |
| Macrolex ® Rot B | No | 100 | 0 |

What is claimed is:

1. A dye of the formula (I)

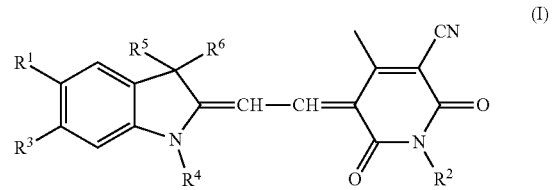

wherein:
  $R^1$ is hydrogen, halogen, COOH or $COOR^7$,
  $R^2$ is hydrogen or is $C_1$-$C_4$-alkyl, optionally mono- to trisubstituted, identically or differently, by halogen and/or hydroxyl,
  $R^3$ is hydrogen, halogen, CN, COOH or $COOR^8$,
  $R^4$ is $C_1$-$C_4$-alkyl or phenyl,
  $R^5$ and $R^6$ are each independently $C_1$-$C_4$-alkyl, and
  $R^7$ and $R^8$ are each independently $C_1$-$C_4$-alkyl
wherein $R^1$ and $R^2$ are not both hydrogen.

2. The dye of claim 1, wherein:
  $R^1$ is hydrogen, fluorine, chlorine, COOH or $COOR^7$,
  $R^2$ is hydrogen, methyl, ethyl, n-propyl, isopropyl, n-butyl, isobutyl or tert-butyl, hydroxymethyl, hydroxyethyl or $CF_3$,
  $R^3$ is hydrogen, fluorine, chlorine, CN or $COOR^8$,
  $R^4$ is methyl or phenyl,
  $R^5$ and $R^6$ are each independently methyl or ethyl, and
  $R^7$ and $R^8$ are each independently methyl or ethyl,
wherein $R^1$ and $R^2$ are not both hydrogen.

3. The dye of claim 1, wherein:
  $R^1$ is hydrogen, fluorine, chlorine or $COOCH_3$,
  $R^2$ is n-butyl, isobutyl, tert-butyl or hydroxyethyl,
  $R^3$ is hydrogen, fluorine or chlorine, and
  $R^4$, $R^5$ and $R^6$ are each methyl
wherein $R^1$ and $R^2$ are not both hydrogen.

4. The dye of claim 3, wherein $R^1$ and $R^3$ are not both hydrogen.

5. A method for the bulk colouration of plastics, the method comprising coloring plastic with one or more dyes of claim 1.

6. The method of claim 5, wherein the plastic is one or more plastics selected from vinyl polymers, polyesters and polycarbonates.

7. The method of claim 6, wherein the plastic is polystyrene, polymethyl methacrylate (PMMA), polyethylene terephthalate or polycarbonate.

8. The method of claim 5, wherein the dye is used in an amount from 0.0001 to 1 percent by weight, based on the amount of plastic.

9. A method for the bulk colouration of plastics, the method comprising contacting the dye of claim 1 with one or more plastics, melting the plastic, and homogenizing the plastic and the dye.

10. The method of claim 9, wherein:
    the contacting comprises mixing or grinding the dye with the plastic; and
    the plastic is in the form of granules.

11. The method of claim 5, comprising mixing the one or more dyes of claim 1 with one or more molten plastics, and homogenizing the mixture.

12. The method of claim 5, wherein the plastic is polymethyl methacrylate (PMMA), and the method comprises mixing or dissolving the dye with one or more methyl methacrylate monomers, and polymerizing the monomers in the presence of one or more polymerization catalysts.

13. A colored plastic composition comprising one or more dyes of claim 1.

14. The plastic composition of claim 11, wherein the plastic comprises polystyrene; polymethyl methacrylate, polyethylene terephthalate, or polycarbonate.

15. A moulding comprising one or more plastic compositions of claim 14.

16. A method for producing the dye according to claim 1, the method comprising:
    contacting one or more aldehydes of the formula (II)

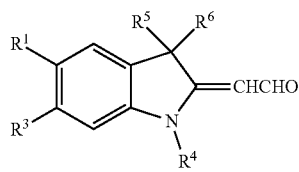
(II)

in which $R^1$, $R^3$, $R^4$, $R^5$ and $R^6$ have the definitions specified in claim 1, with one or more compounds of the formula (III)

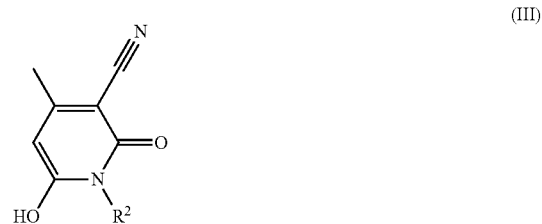
(III)

in which $R^2$, $R^7$ and $R^8$ have the definitions specified in claim 1.

17. A dye of the formula (I)

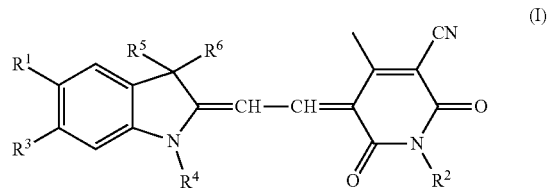
(I)

wherein:
$R^1$ is hydrogen, fluorine, chlorine or $COOCH_3$,
$R^2$ is n-butyl, isobutyl, tert-butyl or hydroxyethyl,
$R^3$ is hydrogen, fluorine or chlorine, and
$R^4$, $R^5$ and $R^6$ are each methyl, and
$R^7$ and $R^8$ are each independently alkyl,
wherein $R^1$ and $R^3$ are not both hydrogen.

\* \* \* \* \*